United States Patent [19]

Charlton

[11] Patent Number: 4,734,375
[45] Date of Patent: Mar. 29, 1988

[54] ION SPECIFIC TEST METHOD

[75] Inventor: Steven C. Charlton, Elkhart, Ind.

[73] Assignee: Miles Laboratories, Inc., Elkhart, Ind.

[21] Appl. No.: 493,969

[22] Filed: May 12, 1983

Related U.S. Application Data

[63] Continuation-in-part of Ser. No. 347,265, Feb. 9, 1982, abandoned, which is a continuation-in-part of Ser. No. 153,883, May 27, 1980, abandoned.

[51] Int. Cl.$^4$ .................... G01N 21/78; G01N 33/52
[52] U.S. Cl. ........................ 436/74; 422/56; 422/57; 436/79; 436/169; 436/172
[58] Field of Search ........... 422/56, 57, 58; 436/73, 436/79, 74, 172, 169; 524/17; 204/418, 296

[56] References Cited

U.S. PATENT DOCUMENTS

| | | | |
|---|---|---|---|
| 3,092,465 | 6/1963 | Adams, Jr. et al. | 422/56 |
| 3,368,872 | 2/1968 | Natelson | 422/56 X |
| 3,562,129 | 2/1971 | Simon | 204/195 M |
| 3,616,251 | 10/1971 | Lecco et al. | 422/56 X |
| 3,630,957 | 12/1971 | Rey et al. | 422/56 X |
| 3,635,679 | 1/1972 | Bloch et al. | 436/169 X |
| 3,767,553 | 10/1973 | Brown, Jr. et al. | 524/17 X |
| 3,957,607 | 5/1976 | Simon et al. | |
| 3,992,158 | 11/1976 | Przybylowicz et al. | 422/58 X |
| 4,003,707 | 1/1977 | Lubbers et al. | |
| 4,061,468 | 12/1977 | Lange et al. | 422/56 |
| 4,225,410 | 9/1980 | Pace | 422/98 X |
| 4,231,754 | 11/1980 | Vogelhut | 422/56 X |
| 4,269,392 | 4/1981 | Lee | 422/56 X |
| 4,272,484 | 6/1981 | Lubbers | 422/68 |
| 4,272,485 | 6/1981 | Lubbers | 422/68 X |
| 4,367,072 | 1/1983 | Vogtle et al. | 436/501 |

FOREIGN PATENT DOCUMENTS

| | | |
|---|---|---|
| 1093641 | 1/1981 | Canada . |
| 1116696 | 1/1982 | Canada . |
| 2842862 | 4/1980 | Fed. Rep. of Germany ........ 436/74 |

OTHER PUBLICATIONS

Feinstein et al., "Proc. Nat. Acad. Sci., U.S.A.", vol. 68, No. 9, pp. 2037–2041, Sep. 1971.
Kusnir et al., Chemical Abstracts, vol. 82, 1975, No. 51257q.
Sumiyoshi et al., Chemical Abstracts, vol. 89, 1978, No. 89:55833s.
Pretsch et al., Research Development, Mar. 1974, pp. 20–23.
B. C. Pressman, "Alkali Metal Chelators—the Ionphores", from *Inorganic Biochemistry*, 1:203–205, Elsevier Scientific Publishing Company, (1973).
Rompps Chemi Lexikon, 8th Ed., vol. 3, Franck Publishing, (1983).
I. M. Kolthoff, "Application of Macrocyclic Compounds in Chemical Analysis," *Analytical Chemistry*, 51:1R–22R, (1979).
M. Takagi et al., "A Novel Colorimetric Reagent for Potassium Based on Crown Ether Formation," *Analytical Letters*, 10:1115–1122, (1977), (citation 190 of E3).
E. S. Hyman, "A Color Reaction of Neutral Cation Carriers of Ionophores," *Biophys. Soc. Abstr.*, 72a (1970), (citation 23 of E4).

*Primary Examiner*—Barry S. Richman
*Assistant Examiner*—Robert J. Hill, Jr.
*Attorney, Agent, or Firm*—Roger N. Coe

[57] ABSTRACT

A test means for detecting the presence of a specific ion in an aqueous test sample and for determining its concentration comprises a substantially nonpolar, nonporous carrier matrix which is incorporated with an ionophore capable of selectively forming a complex with the ion under analysis. In addition, a counterion reporter substance is provided separately, which is capable of producing a detectable response, such as a change in or appearance of color or fluorescence in the carrier matrix. In use, the test sample containing the counterion reporter substance is contacted with the test means, the test means is washed and any detectable response associated with the test means is determined.

4 Claims, 6 Drawing Figures

ION SPECIFIC TEST METHOD

1. RELATED APPLICATIONS

The present application is a continuation-in-part of U.S. application Ser. No. 347,265, filed Feb. 9, 1982, now abandoned, which is in turn a continuation-in-part of U.S. application Ser. No. 153,883, filed May 27, 1980 and now abandoned.

2. INTRODUCTION

The present invention relates to the measurement of ions, in particular ions in aqueous solution, and to a test means or device for performing such measurements. The invention provides a quick, facile way of assaying such ions whereby results are available to the assayist momentarily after merely contacting a test sample solution with the test means or device and washing the test device. There is no need for cumbersome, expensive electronic equipment such as ion-specific electrodes, flame photometers, atomic absorption spectrophotometers or the like. Nor is it necessary to resort to time-consuming wet chemistry techniques such as titration and other laboratory procedures. The present invention enables the analyst to merely contact the test sample with a strip device or similar test means configuration, wash and observe any color change associated with the surface of the test means.

The determination of aqueous ion concentration has application in numerous technologies. In the water purification art, calcium concentration must be carefully monitored to assess the degree of saturation of an ion exchange resin deionizer. Measurement of sodium and other ions in seawater is important in the preparation of drinking water aboard a ship at sea. Measurement of the potassium level in blood aids the physician in diagnosis of conditions leading to muscle irritability and excitatory changes in myocardial function. Such conditions include oliguria, anuria, urinary obstruction and renal failure due to shock.

Needless to say, a quick, facile method for determining ion concentration would greatly enhance the state of these technologies, as well as any others where such rapid, accurate determinations would be beneficial. Thus, for example, if a medical laboratory technician could accurately measure the potassium or calcium level of a serum or whole blood sample in a matter of seconds or minutes, not only would such rapid results aid the physician in diagnosis, but also laboratory efficiency would increase manyfold.

3. BACKGROUND OF THE INVENTION

Prior to the present invention, methods for determining ions in solution included flame photometry, atomic absorption photometry and ion-specific electrodes. The use of certain compounds and compositions which selectively isolate certain ions from the sample solution has become popular in ion-specific electrodes. These substances, known as ionophores, have the capability of selectively isolating ions from their counterions thereby causing a charge separation and a corresponding change in electrical conductivity in the phase containing the ionophore. Illustrative of the ion/ionophore phenomenon include ion assays utilizing membrane electrodes, liquid/liquid partitioning and fluorescence.

3.1 Ion-Specific Electrodes

When two solutions having different concentrations of ions are separated by an electrically conductive membrane, an electrical potential (EMF) is generated. The EMF developed by such a system is a function of concentration or ionic activity. This phenomenon is expressed mathematically by the well-known Nernst Equation $$\epsilon = \frac{RT}{nF} \ln \frac{\gamma_1 c_1}{\gamma_2 c_2} \quad (1)$$

in which $\epsilon$ is the EMF of the particular system, F is the Faraday Constant $[23,062.4 \pm 0.003$ calories (volt equiv.)$^{-1}$], R is the gas constant, T is the temperature in °C. and $\gamma$ and c are respectively, the activity coefficients and molal concentrations of the ion under study, the subscript 1 designates the solution on one side of the membrane, the subscript 2 denoting the solution on the other side, and n is the number of electrons transferred in the reaction.

In such membrane separation cells, the membrane can be a simple fritted glass barrier, allowing a small but measurable degree of ion diffusion from one solution to the other. Alternatively, a nonporous, electrically nonconductive film, such as polyvinyl chloride, impregnated with an ionophore can be employed. In the absence of the ionophore the film is an insulator and no EMF can be measured; when blended with an ionophore, charged ions are bound to the film and a small, measureable current can be induced to flow. Because the ionophore is selective in its affinity, and thus will bind only certain specific ions, such cells are ion selective. Any measurable EMF is due solely to the presence of those ions.

Thus, a cell for determining potassium ion can be produced through use of an ionophore specific for $K^+$, e.g. valinomycin. In the presence of potassium ($K^+$), valinomycin produces a conductive path across a membrane by binding and transporting $K^+$, thus allowing a small current to flow. A reference concentration of $K^+$ is placed on one side of the membrane and the test sample on the other. The EMF developed is measured and used to calculate the unknown concentration from equation (1). Because $K^+$ binds to the valinomycin membrane, the conductive path only appears for $K^+$. Therefore, the only EMF developed is attributable solely to the $K^+$ concentration gradient across the membrane.

The current flowing across the membrane is so small that no significant quantity of $K^+$ or counter-ion is transported through it. Electrical neutrality of the membrane can be maintained either by a reverse flow of hydrogen ions, or by a parallel flow of $OH^-$. This anion effect can reduce the specificity of the electrode towards the intended ion and is an interference to be minimized.

A major difficulty in the use of such ion-selective electrodes has been the marked reduction of accuracy and speed of response over time. Further, small changes in ion concentration produce such small changes in EMF that sophisticated voltmeter equipment is required.

It has been known that certain antibiotics, such as valinomycin, have an affect on the electrical properties of phospholipid bilayer membranes (biological membranes), such that these antibiotics solubilize cations within the membrane, in the form of mobile charged couples, thereby providing a "carrier" mechanism by which cations can cross the insulating hydrocarbon interior of the membrane. Such complexes have the sole purpose of carrying the charge of the complex through the membrane such that a voltage differential can be determined between solutions on either side of the membrane.

U.S. Pat. No. 3,562,129 describes the use of porous membranes impregnated with macrocyclic derivatives of amino and oxy-acids in ion-sensitive electrodes. Materials used to form the membrane are glass frits and other porous membranes. Such electrodes are said to be effective in measuring ion activities.

U.S. Pat. No. 4,053,381, issued to Hamblen, et al. discloses similar technology, and utilizes an ion specific membrane having ion mobility across it.

3.2 Liquid/Liquid Partitioning

Another known application of ionophores in ion determination is through liquid/liquid partitioning. In this procedure, a hydrophobic ionophore is dissolved in an organic solvent immiscible with water. Eisenman et al., J. Membrane Biol., 1:294–345 (1969) disclose the selective extraction of cations from aqueous solutions into organic solvents via macrotetralide actin antibiotics. This technique involves merely shaking an organic solvent phase containing the antibiotics with aqueous solutions containing cationic salts of lipid-soluble colored anions, such as picrates and dinitrophenolates. The intensity of color of the organic phase is then measured spectrophotometrically to indicate how much salt has been extracted. Phase transfer has also been studied by Dix et al., Angew. Chem. Int. Ed. Engl., 17:857 (1978) and in reviews including Burgermeister et al., Top. Curr. Chem., 69:91 (1977); Yu et al., "Membrane Active Complexones," Elsevier, Amsterdam (1974); and Duncan "Calcium in Biological Systems," Cambridge University Press (1976).

Sumiyoshi, et al., Talanta, 24, 763–5 (1977) describes another method useful for determining $K^+$ in serum. In this technique serum is deproteinated by trichloroacetic acid, an indicator dye is added, and shaken with a solvent such as chloroform containing valinomycin.

Partitioning of a compound is rapid and effective between liquids, as shown by Eisenman, because of the mobility of the ionophore carrier and ions, which allows the transported species to diffuse rapidly away from the interface. Such a mechanism is normally impossible in the solid phase, because of the rigidity, immobility and essentially zero diffusion of materials in a solid phase.

3.3 Fluorescent Anions

Yet another approach to the measurement of ion activity in aqueous solutions utilizes fluorescent anions. Feinstein, et al., Proc. Nat. Acad. Sci. U.S.A., 68, 2037–2041 (1971). It is stated that the presence of cation/ionophore complexes in organic solvents are known, but that complex formation in purely aqueous media had theretofore not been detected. Feinstein, et al., demonstrated the existence of such complexes in water through the use of the fluorescent salts 1-anilino-8-naphthalene sulfonate and 2-p-toluidinyl sulfonate.

It was found that interaction of the ionophore/cation complexes with the fluorescent dyes produced enhanced fluorescence emission, increased lifetime and polarization, and significant blue-shift at the emission maxima of the fluorescence spectrum. At constant concentrations of ionophore and fluorophore, the intensity of fluorescence emission was found to be a function of cation concentration.

3.4 Summary

To summarize the background of technological developments leading up to the present invention, many methods are known for assaying ions in solution. Instrumental methods include such sophisticated techniques as ion-specific potentiometry, flame photometry and atomic absorption photometry. The use of ionophores which selectively complex with specific ions has led to three basic approaches: ion selective electrodes, liquid/liquid partitioning and fluorescence enhancement.

None of these approaches, however, affords the assayist simple, fast analysis results through contacting a test sample solution with a test means or device. The present invention, on the other hand, permits the assayist to merely contact the sample with a dip-and-read test strip or device of similar configuration, wash and observe a change in color or other detectable response associated with the surface of the test strip.

5. SUMMARY OF THE INVENTION

The present invention resides in the discovery of a new test means for detecting the presence of a specific ion in aqueous test sample and to determining its concentration. The test means comprises a substantially nonpolar, nonporous carrier matrix which is incorporated with an ionophore capable of selectively forming a complex with the ion under analysis. In addition, the test requires the addition of a counterion reporter substance to the sample which is capable of producing a detectable response, such as a change in or appearance of color or fluorescence.

A test device incorporating the test means comprises an elongated support member, such as a plastic film, to one flat side of which is affixed the test means.

In use, the counterion reporter substance is added to the test sample, and the sample is contacted with the test means or device. After washing the test device, the presence and/or concentration of the ion is then determined by observing any detectable response associated with the surface of the test device.

The test means and device of the present invention provide rapid results, sufficient detectable response forming in most instances in at least a few minutes. Moreover, no cumbersome, expensive testing equipment is required in addition to the present invention.

Moreover, it has been found that the color or other response produced in the test means is stable, in some instances for a period of days, such that a number of used test means can be set aside for reading at some future time.

6. DEFINITIONS

Certain terms used in the present discussion should be mentioned. Thus, the following definitions are provided to clarify the scope of the present invention, and to enable its formulation and use.

6.1 The term "ionophore" includes molecules capable of selectively forming a complex with a particular ion to the substantial exclusion of others. For example the cyclic polypeptide, valinomycin, binds selectively to potassium ions in solution to form a cationic complex. Also included in the term are crown ethers, cryptands and podands.

6.2 As used herein, "substantially nonpolar" is intended as meaning that quality of a substance not to exhibit a substantial dipole moment or electrical polarity. In particular, it includes nonionic substances, and substances which are dielectric. 6.3 The term "nonporous" is intended to mean substantially impervious to the flow of water. Thus a nonporous carrier matrix is one which precludes the passage of water through it, one side to the other. For example, a polyvinyl chloride film would be considered for the purposes herein as being nonporous.

6.4 A "reporter substance" is a counterion which is capable of interacting with an ionophore/ion complex to produce a color change or other detectable response in the test means. Thus, the reporter can be an ionic dye such that when the dye is in its ionized state it is a counterion, i.e., opposite in charge, to the ion to be analyzed. Some examples of these are Erythosin B, and 2,6-dichloroindophenol sodium salt. The reporter also includes ionized form of phenolic compounds, such as p-nitrophenol, which are relatively colorless in the non-ionized state, but which are colored upon ionization. The counterion reporter substance can also be one which can trigger a detectable response together with other components. For example, the iodide ion can produce a detectable response by interacting with the ionophore/ion complex in the presence of starch and an oxidizing agent in the test means.

6.5 By "interacting" is meant by coaction between a reporter substance and an ionophore/ion complex which leads to a detectable response. Where the reporter is an anionic dye added to the test sample, it interacts with the cationic ionophore complex leading to substantial transfer of anionic dye to the carrier matrix, despite the substantial nonporosity of the matrix, thereby producing a color in the matrix in response to the cation.

6.6 The expression "detectable response" is meant as a change in or occurence of a parameter in a test means system which is capable of being perceived, either by direct observation or instrumentally, and which is a function of the presence of a specific ion in an aqueous test sample. Some detectable responses are the change in or appearance of color, fluorescence, reflectance, pH, chemiluminescence and infrared spectrum.

7. THE TEST

The present test comprises three basic elements: a substantially nonpolar carrier matrix; an ionophore incorporated with the matrix; and a separately provided counterion reporter substance. When an aqueous test sample contains an ion capable of specifically complexing with the ionophore, the ion can then enter the matrix and the ionophore/ion complex can interact with the counterion reporter substance, thereby producing a detectable response associated with the matrix.

7.1 The Carrier Matrix

In order for the test means to provide a detectable response solely as a result of the presence of a specific ion, it is necessary that all other ions be excluded from entering the carrier matrix. This is because it is the ionophore/ion complex which causes the detectable response due to the association of the counterion reporter substance with the carrier matrix. Accordingly, the carrier matrix must be fabricated from a material which is both nonpolar and nonporous. Exemplary of such materials are films of such polymers as polyvinyl fluoride, polyvinyl chloride, vinyl chloride/vinyl acetate copolymer, vinyl chloride/vinylidene chloride copolymer, vinyl chloride/vinyl acetate/vinyl alcohol terpolymer, vinylidene chloride/acrylonitrile copolymer, and polyurethane. Of course, many other polymeric materials would be suitable for use in the present invention, and the identification of such materials would be well within the skill of the art, given the present disclosure. Preferred matrix formulations include plasticizers well known in the art such as diphenthyl phthalate, tris-2-ethylhexylphosphate and di-2-ethylhexylsebacate, used in the examples herein.

Likewise, it is required that the carrier matrix be nonporous and nonpolar, again because the ion should not be able to penetrate the matrix unless it is that particular ion for which the ionophore has complexing affinity. The concept of a nonporous matrix, of course, does not exclude microscopic porosity. It is clear from the foregoing remarks as well as the very nature of the invention, that some porosity could be possible, provided the analyte ion be precluded from permeation of the carrier matrix to a sufficient degree that no detectable response is formed unless the ionophore is present.

The composition of the carrier matrix in the present invention is to be carefully distinguished over prior art test means whereby porous materials such as paper were used. In that type of device, it is required that any test sample to which the device is exposed be capable of permeating the entire reagent area. Such test devices function on entirely different principles from the present one, and a paper carrier matrix is not considered as within the scope of the present invention unless such paper matrix be rendered substantially nonpolar and nonporous, i.e., such as by polymer impregnation.

Thus, the carrier matrix is one which is not wetted by water, i.e., one which precludes substantial penetration by the aqueous test sample. Moreover, it is intended that the ionophore becomes virtually insoluble due to being entrapped with the carrier matrix. The requirement of nonporosity of the carrier matrix is to preclude dissolution or leaching of ionophore as well as to prevent permeation by test sample components other than the ionic analyte.

7.2 Ionophores

The ionophore element of the present invention is indeed a concept which is broad in scope, as characterized by the definition of the term in paragraph 6.1, supra. It includes multidentate cyclic compounds which contain donor atoms in their cyclic chains. Such multidentate cyclic compounds can be monocyclic or polycyclic. Alternatively, the ionophore can be an open chain containing donor atoms. Thus, included in the term are monocyclic systems which are ion-specific, termed coronands; polycyclic ion-specific compounds known as cryptands; and open chain structures which are known as podands capable of selectively complexing with ions.

7.2.1 Coronands

The coronands are monocyclic compounds which contain donor atoms which are electron rich or deficient and which are capable of complexing with particular cations and anions because of their unique structures. Included in this term are the crown ethers in which the monocyclic chain contains oxygen as the donor atoms. Other coronands are compounds which contain an assortment of electron rich atoms such as oxygen, sulfur and nitrogen. Because of the unique sizes and geometries of particular coronands, they are adaptable to complexing with various ions. In so complexing, the electron rich atoms, such as the oxygens in a crown ether, orient towards the electron deficient cation. The carbon atom segments of the chain are simultaneously projected in a direction outwards from the ion. Thus, the resultant complex is charged in the center but is hydrophobic at its perimeter.

7.2.2 Cryptands

The cryptands are the polycyclic analogues of the coronands. Accordingly, they include bycyclic and tricyclic multidentate compounds. In the cryptands, the cyclic arrangement of donor atoms is three dimensional in space, as opposed to the substantially planar configuration of the coronand. A cryptand is capable of virtually enveloping the ion in three dimensional fashion and, hence, is capable of strong bonds to the ion in forming the complex. Like in the coronands, the donor atoms can include such atoms as oxygen, nitrogen and sulfur.

7.2.3 Podands

Ions can also be selectively complexed with noncyclic compounds. For example, a linear chain which contains a regular sequence of electron rich atoms such as oxygen has the capability of associating with positively charged ions to form complexes, not entirely unlike the coronands and cryptands. The main structural difference between podands and the other two ionophores is the openness of the structure. Thus, podands can be subcategorized into monopodands, dipodands and tripodands, and the like. A monopodand, therefore, is a single organic chain containing donor atoms, a dipodand is two such chains capable of variable special orientation, and a tripodand is three chains attached to a central atom.

7.2.4 Specific Ionophores

Some of the ionophores which have been found to be especially useful with the instant invention are tabulated herein along with the cations with which they are capable of selectively complexing.

| Ionophore | Cation |
|---|---|
| Valinomycin | $K^+$ |
| 4,7,13,16,21-Pentaoxa-1,10-diaza-bicyclo[8,8,5]tricosane [Kryptofix 221) | $Na^+$ |
| 4,7,13,16,21,24-Hexaoxa-1,10-diaza-bicyclo[8,8,8]hexacosane (Kryptofix 222) | $K^+$ |
| 4,7,13,18-Tetraoxa-1,10-diaza-bicyclo[8,5,5]eicosane (Kryptofix 211) | $Li^+$ |
| 12-Crown-4 | $Li^+$ |
| 15-Crown-5 | $Na,K^+$ |
| 18-Crown-6 | $K^+$ |
| Dibenzo-18-crown-6 | $K^+$ |
| Dicyclohexano-18-crown-6 | $K^+$ |

Kryptofix is a registered trademark of E. Merck, Darmstadt, Germany.

7.3 The Reporter Substance

Given the presence of the ion of interest in the test solution, it is the counterion reporter substance which provides the detectable response by interacting with the ionophore/ion complex. The reporter substance can range in composition from a single compound, such as a chromogenic counterion, to a mixture of reactive species which produce a detectable product when their reaction chain is triggered by the interaction of the counterion with the complex. Thus, it can be seen that when no analyte ion is present the reporter substance remains dormant; no detectable response associated with the carrier matrix is observed. Alternatively, when the particular ion under surveillance is present, it is enabled by the ionophore to enter the carrier matrix to form a complex, which complex interacts with the counterion reporter substance and induces it to associate with the carrier matrix and produce a detectable change in the matrix.

In the case where the reporter is a single compound, it can include a salt or other dissociable compound, such that upon dissociation a colored ionic species is formed. Depending on the charge of the analyte ion, an ionic reporter is chosen such that the colored ion is opposite in charge to the analyte. Also useful is a dissociable compound in which the counterion to the analyte is fluorescent. Examples of such chromophoric and fluorophoric reporter substances are the ionic forms of dichlorophenolindophenol, fluorescein and its derivatives, 8-anilino-1-naphthalenesulfonic acid, Erythrosin B, Orange IV, Phloxine B, and Eosin Y. Structures of Erythrosin B, Phloxine B and Eosin Y are given in "Aldrich Handbook of Fine Chemicals", Aldrich Chemical Company, Milwaukee (1983). The structure of Orange IV can be found in "The Merck Index", 9th ed., Merck & Co., Inc. Rahway (1976).

Where the counterion reporter substance triggers a mixture of reactive species the carrier matrix, great latitude is possible in selecting an appropriate combination of ingredients. For example, one system could be iodide ion, starch and an oxidizing agent. Such a system could be utilized in a test means in which the carrier matrix contains (in addition to ionophore) starch and the oxidizer. Iodide could then be added to the test sample. In the presence of an analyte ion, formation of the ion/ionophore complex would induce iodide to associate with the matrix, whereupon it would be converted to free iodine, thus indicating a positive test.

Yet another example of a reaction sequence useful as the reporter substance is one which involves the dissociation of a proton from a phenol, thus initiating a coupling reaction to form a colored product. The so-called Gibbs Reaction is typical of such a reaction sequence, in which 2,5-cyclohexadiene-1-one-2,6-dichloro-4-chloroimine couples with a phenol to form a colored reaction product In this reaction sequence R can be any 2,3,5 and/or 6 position substituent which will not hinder the overall reaction sequence. Thus R is H, lower alkyl or aryl, or R can form a fused ring system at either the 2,3- or 5,6-positions. By "lower alkyl is meant an alkyl group having 1-4 carbon atoms. Thus, R includes methyl, ethyl, n-propyl, isopropyl, n-butyl, sec-butyl, and tert-butyl.

Another utilization of the Gibbs chemistry involves compounds having a structure such as (III) as the counterion reporter.

8. THE TEST DEVICE

The test means described above can be used by itself or it can be mounted at one end of an elongated support member, the other end serving as a handle. Such a test device can be held at the handle end, while the other end bearing the test means is contacted with the test sample.

Useful materials for the support member include films of a myriad of plastics or polymers. Examples include such polymeric materials as cellulose acetate, polyethylene terephthalate, polycarbonates and polystyrene. The support can be opaque or it can transmit light or other energy. Preferred supports include transparent materials capable of transmitting electromagnetic radiation of a wavelength in the range of about 200 nanometers (nm) to 900 nm. The support need not, of course, transmit over the entire 200-900 nm region, although for fluorometric detection of analytical results it is desirable that the support be transparent over a band wider than, or at least equal to the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics.

To prepare a test device of the present invention, a small rectangle of the test means, i.e., a carrier matrix incorporated with an ionophore and possibly other ingredients, is affixed to an elongated support member having an upper substantially flat face, such as an oblong piece of polystyrene film. The test means piece is affixed to the flat face at one end, leaving the other end of the polystyrene to serve as a convenient handle.

The test means can be affixed by any means compatible with the intended use. A preferred method is by using a double faced adhesive tape between the test means, square and the support member. One such tape is known as Double Stick®, available from 3M Company.

9. USE OF THE INVENTION

The test means and device of the present invention can be adapted for use in carrying out a wide variety of chemical analyses, not only in the field of clinical chemistry, but in chemical research and chemical process control laboratories. They are well suited for use in clinical testing of body fluids, such as blood, blood serum and urine, since in this work a large number of repetitive tests are frequently conducted, and test results are often needed a very short time after the sample is taken. In the field of blood analysis, for example, the invention analysis for many of the ionic blood components of clinical interest.

The test means (and test device) is used by contacting it with the test sample in the presence of a counterion reporter substance, washing the test means and observing a detectable response associated with the surface of the test means. In a typical analytical procedure in which the reporter substance is first added to the test sample, a portion of test sample is placed on the test means for a sufficient period of time (such as several minutes). After that the excess sample, containing counterion not associated with the test means is removed, such as by washing in a gentle stream of water with subsequent blotting with tissue paper.

If the ion under analysis is present in the test sample, the complex of ionophore and ion in the carrier matrix will interact with the counterion reporter substance in the test sample, and a detectable response will appear associated with the matrix. Where the reporter substance, for example, is a dissociable salt producing a colored counterion of the analyte, an observable color will form in the carrier matrix. Where the reporter substance is a fluorophore such as fluoroscein, a fluorescence spectrophotometer can be utilized to measure the detectable response formed in the test means (here, the appearance of or change in fluorescence). Other techniques useful in observing a detectable response include reflectance spectrophotometry, absorption spectrophotometry and light transmission measurements.

When the test sample is blood serum, transmission techniques can be used to detect and quantify the presence of any reaction products, the formation of which serves as the detectable response. In this case radiant energy such as ultraviolet, visible or infrared radiation, is directed onto one surface of the test means and the output of that energy from the opposite surface is measured. Generally, electromagnetic radiation in the range of from about 200 to about 900 nm has been found useful for such measurements, although any radiation permeating the test means and which is capable of signifying the occurrence or extent of the response can be used.

Various calibration techniques are applicable as a control for the analysis. For example, a sample of analyte standard solution can be applied to a separate test means as a comparison or to permit the use of differential measurements in the analysis.

10. EXAMPLES

The following Examples are provided to further assist the reader in making and using the present invention. Thus, preferred embodiments are described in experimental detail and analyzed as to results. The Examples are meant to be illustrative only, and are in no way intended as limiting the scope of the invention described and claimed herein.

10.1 Preparation of a Test Means Responsive to Potassium

In the experiment described by this example, a test means was prepared and tested for its ability to quantitatively determine, as determined by reflectance methods, the presence of potassium in a liquid sample.

A solution was prepared containing the following components:

| Component | Quantity | Final Concentration (g/100 ml of solution) |
|---|---|---|
| Polyvinyl-chloride (PVC) | 38.4 milligrams (mg) | 3.84 |
| Dipentyl-phthalate (DPP) | 129.6 mg | 12.96 |
| Valinomycin | 4.0 mg | 0.4 |
| Tetrahydro-furan (THF) | 0.87 milliliter (ml) | 89.0 |
| Total value | 1.0 ml | 100 mls |

DPP served as a plasticizer for the PVC.

One ml of this solution was placed on a sheet of transparent, water impervious, polyester film, Gel Bond TM (marine Colloids, Inc.), and spread to a depth of 0.254 mm using a conventional doctor blade. Scotchpar 70 GAB 2S (3M Corporation) could be used in lieu of Gel Bond. Other suitable support member materials are Eastman A150 polyester and acylonitrile copolymers, such as those comprising about 70% by weight of acrylonitrile, 20–30% of methyl acrylate or styrene and 0–10% of butadiene. Other suitable support members include cellulose acetate butyrate and cellulose acetate propionate. A film of approximately 30 square centimeters (cm) having a 25 microns thickness was produced. The film was air dried for approximately 30 minutes.

For reflectance measurements the polyester film was then cut into 1 cm squares and the uncoated side faced onto a light scattering polystyrene support (white Trycite ®) with 3M brand double faced adhesive.

Test samples for use in assessing the performance of the test means were prepared by adding KCl to aliquots of a solution containing 35.6 mM (millimolar) tris-(hydroxymethyl)amino methane ("tris-HCl") and 8.80 mM Erythrosin-B (pH 7.2). These solutions had potassium concentrations of 0.133, 0.2, 0.3, 0.4, 0.5, 0.6, 0.75, 0.9 and 1.1 mM, respectively.

The efficacy of the test means in detecting potassium in the test sample was studied. A portion of each solution sufficient to provide a dome of liquid was placed on a respective square of the test means film. After 4 minutes the excess liquid was removed by a gentle stream of water and the element gently blotted with tissue paper. The retained dye, associated with the test means, was quantified from percent reflectance (%R) measurements at 530 nanometers (nm) using a reflectance spectrometer. Readings taken on test solutions of 0.2 and 0.5 mM potassium concentrations were used to calibrate the spectrometer.

The readings obtained by this analytical procedure were in the form of % R units which were mathematically converted to potassium concentration using the Kubelka-Munk equation and the calibration values, ($K^+$ units). The observed reflectance measurements and their corresponding $K^+$ concentrations are reported in Table 1.

TABLE 1

| Actual $K^+$ (mM) | (% R) | Observed $K^+$ (mM) |
|---|---|---|
| 0 | 62.9 | 0.03 |
| 0.133 | 40.5 | 0.19 |
| 0.2 | 36.2 | 0.24 |
| 0.3 | 30.7 | 0.35 |
| 0.4 | 27.1 | 0.44 |
| 0.5 | 24.9 | 0.51 |
| 0.6 | 23.0 | 0.58 |
| 0.75 | 19.4 | 0.76 |
| 0.9 | 18.4 | 0.83 |
| 1.1 | 15.9 | 1.02 |

As can be seen from the data, the observed $K^+$ concentrations based on reflectance measurements correlate well with actual $K^+$ concentrations, thus showing that the test means is capable of providing a quantitative detectable response to each of the aliquots tested.

10.2 Capability of Distinguishing Between $K^+$ and $Na^+$

An experiment was conducted to determine whether the test means of Example 10.1 is selective for $K^+$ and not interfered with by the concurrent presence of sodium ion in the test sample.

A test means was prepared as described in Example 10.1 except that it was not affixed to a light scattering support. Test samples were prepared containing KCl and/or NaCl by adding quantities of those salts yielding the concentrations listed below in Table 2 to aliquots of water containing 5 millimolar (mM) Erythrosin B and 50 mM tris-acetate (pH 7.2).

TABLE 2

| Solution | $K^+$ (mM) | $Na^+$ (mM) |
|---|---|---|
| 1 | 0 | 4 |
| 2 | 0 | 10 |
| 3 | 0 | 20 |
| 4 | 0 | 50 |
| 5 | 0 | 100 |
| 6 | 2.2 | 0 |

The analysis of the above-prepared test solutions was performed by the same procedure used in Example I, with the exception that the detectable response was quantified by measuring light absorbance through the test means at 553 nm. Three measurements were made with each solution and the mean value determined.

These were measured in absorbance units which were mathematically converted to potassium concentrations ($K^+$) units, using the first and last entries as calibrating values. These readings and respective observed concentrations are reported in Table 3.

TABLE 3

| Actual $K^+$ (mM) | Actual $Na^+$ (mM) | Absorbance (553 nm) | Observed $K^+$ (mM) |
|---|---|---|---|
| 0 | 4 | 0.063 | 0 |

TABLE 3-continued

| Actual K+ (mM) | Actual Na+ (mM) | Absorbance (553 nm) | Observed K+ (mM) |
|---|---|---|---|
| 0 | 10 | 0.062 | 0 |
| 0 | 20 | 0.063 | 0 |
| 0 | 50 | 0.060 | −0.01 |
| 0 | 100 | 0.057 | −0.03 |
| 2.2 | 0 | 0.547 | 2.2 |

The resultant data shows the test means to provide a quantitative detectable response specifically to the potassium concentration of each of the aliquots tested, whereas no detectable response to sodium alone was observed.

10.3 The Effect of Various Plasticizers on Test Results

An experiment was conducted to determine the utility of plasticizers other than that used in Example 10.1, i.e., dipentyl phthalate. Accordingly, test means were formulated using, as plasticizer tris-2-ethylhexylphosphate (TEP) and di-2-ethylhexylsebacate (DHS) respectively.

The test means films were prepared in accordance with the procedure of Example 10.1 using the following ingredients, in which the plasticizer was TEP or DHS:

| Component | Quantity | Final Concentration (g/100 mls solution) |
|---|---|---|
| PVC | 40 mg | 4 |
| Plasticizer | 100 mg | 10 |
| Valinomycin | 1.5 mg | 0.15 |
| THF | 0.9 ml | 90 |
| Total value | 1 ml | 100 ml |

Test samples for assessing the performance of these test means were prepared by adding KCl to aliquots of an aqueous solution of 40 mM tris-Cl and 10 mM Erythrosin B (pH 7.2). These solutions had final potassium concentrations of 0.2, 0.4, 0.6, 0.8 and 1.1 mM, respectively. One aliquot containing no potassium was set aside as a control.

These test samples were assayed using the test means described above. The procedure was the same as in Example 10.1 except that %R measurements were taken at 540 nm, and the spectrometer was calibrated for readings taken with those aliquots containing 0.4 and 0.8 mM K+. Tests were performed in triplicate and the mean values for each test are reported in Table 4, below, as well as K+ concentrations calculated from the observations.

TABLE 4

| Actual K+ (mM) | TEP | | DHS | |
|---|---|---|---|---|
| | % R | K+ (mM) | % R | K+ (mM) |
| 0 | 39.8 | −0.23 | 62.8 | 0 |
| 0.2 | 33.0 | 0.18 | 41.7 | 0.21 |

TABLE 4-continued

| Actual K+ (mM) | TEP | | DHS | |
|---|---|---|---|---|
| | % R | K+ (mM) | % R | K+ (mM) |
| 0.4 | 29.4 | 0.47 | 34.1 | 0.37 |
| 0.6 | 27.5 | 0.67 | 28.4 | 0.55 |
| 0.8 | 25.9 | 0.86 | 24.4 | 0.71 |
| 1.1 | 24.3 | 1.07 | 20.3 | 1.02 |

Figure 1:
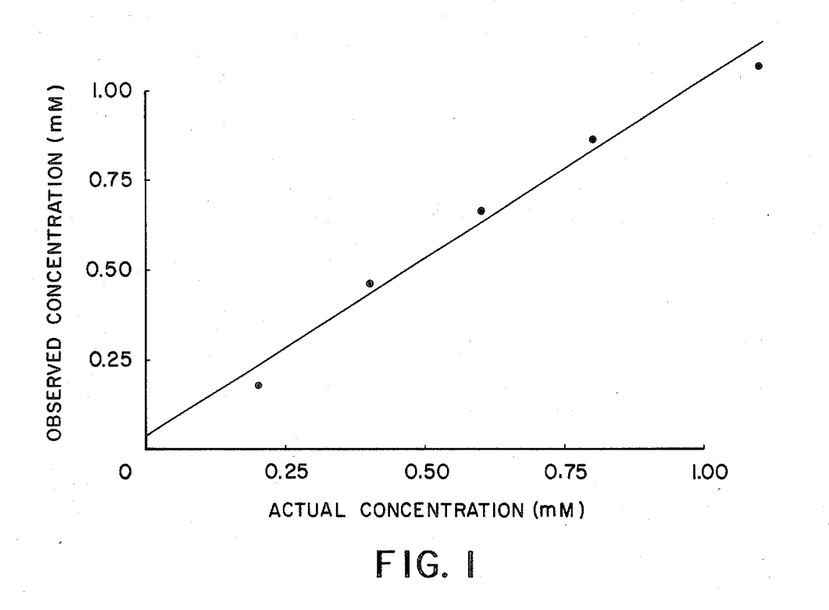
FIG. 1 is a graphical representation of the data using tris-2-ethylhexylphosphate as plasticizer, reported in Table 4.
Figure 2:
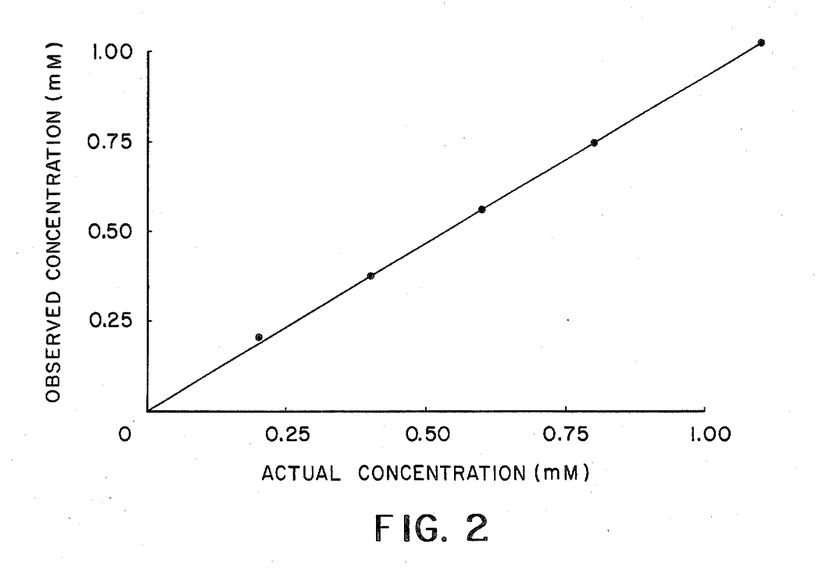
FIG. 2 is a graphical representation of the data using di-2-ethylhexylsebacate as plasticizer, reported in Table 4.
Figure 3:
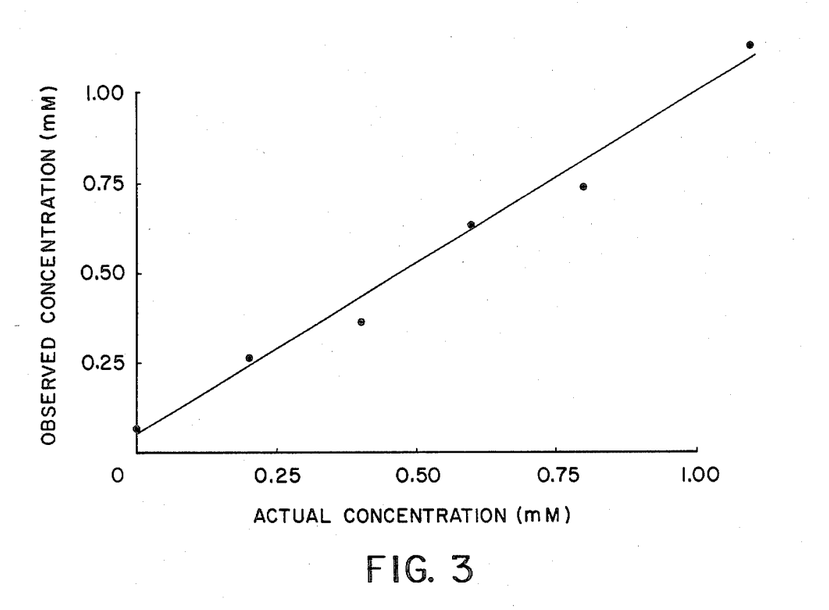
FIG. 3 is a graphical representation of the data using Phloxine B as the counterion, reported in Table 5.
Figure 4:
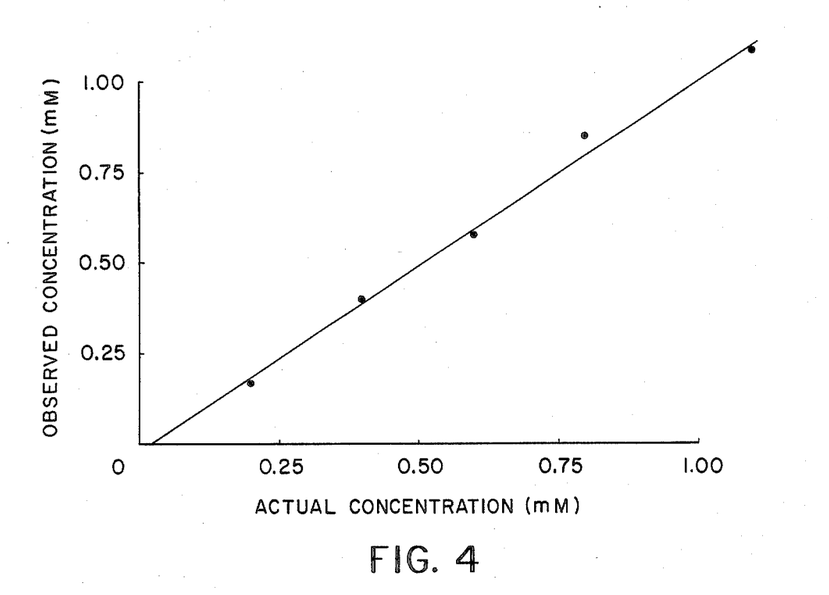
FIG. 4 is a graphical representation of the data using Orange IV as the counterion, reported in Table 5.
Figure 5:
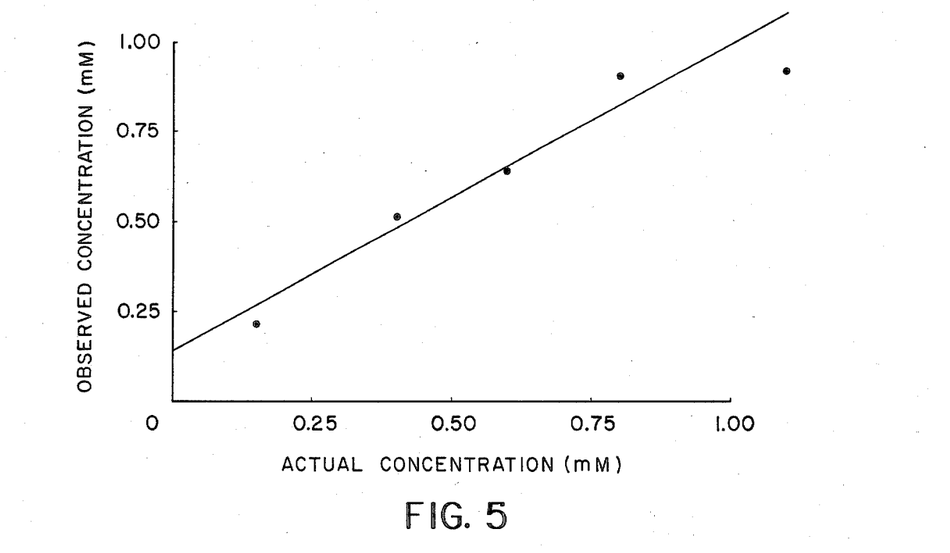
FIG. 5 is a graphical representation of the data, using Eosin Y as the counterion, reported in Table 5.
Figure 6:
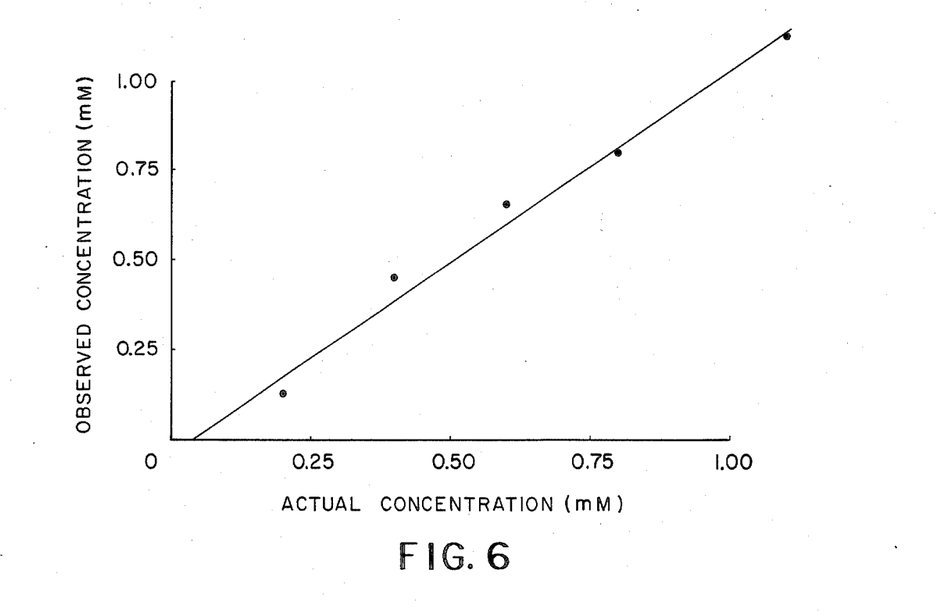
FIG. 6 is a graphical representation of the data, using 2,6-dichlorophenol indophenol (DCPIP) as the counterion, reported in Table 6.

The data of Table 4 is plotted graphically in FIG. 1 (TEP) and FIG. 2 (DHS).

The results of this experiment indicate that test means prepared using TEP or DHS as plasticizers were effective in quantitatively measuring the presence of K+ in a test sample.

10.4 Various Reporter Substances

Experiments were conducted to assess the performance of various reporter substances used as additives to the test sample. The reporter substances tested were ionic forms of 2,6-dichlorophenol indophenol (DCPIP), Orange IV, phloxin B and Eosin Y.

Test means specific for potassium ion were prepared as in Example 10.3 except that dipentylphthalate was used as the plasticizer. Test samples for studying the performance of the test means with various reporter substances were likewise prepared as in Example 10.3 except that four series of aliquots were prepared, each containing a different reporter substance in place of the Erythrosin B of Example 10.3, i.e., 10 mM of DCPIP, Orange IV, Phloxine B and Eosin Y, respectively.

Each series of aliquots was tested for potassium using the test means as in Example 10.3. Depending on which reporter substance was used in the test sample, %R was measured at the following wavelengths:

Phloxine B—550 nm
DCPIP—680 nm
Orange IV—430 nm
Eosin Y—550 nm

The results of this experiment are listed in Table 5 and show excellent correlation between measured and actual K+ concentration with each of the reporter substances studied. The data is presented graphically in FIGS. 3, 4, 5 and 6 for Phloxine B, Orange IV, Eosin Y and DCPIP, respectively.

TABLE 5

| Actual K+ (mM) | Phloxine B | | DCPIP | | Orange IV | | Eosin Y | |
|---|---|---|---|---|---|---|---|---|
| | % R | K+ (mM) | % R | K+ (mM) | % R | K+ (mM) | % R | K+ (mM) |
| 0 | 59.7 | 0.06 | 52.3 | −0.16 | 65.1 | −0.1 | 64.7 | −0.46 |
| 0.2 | 57.0 | 0.26 | 35.3 | 0.10 | 49.9 | 0.17 | 60.9 | 0.21 |
| 0.4 | 55.7 | 0.36 | 25.5 | 0.45 | 42.5 | 0.41 | 59.4 | 0.51 |
| 0.6 | 52.7 | 0.63 | 22.0 | 0.66 | 38.8 | 0.57 | 58.8 | 0.63 |
| 0.8 | 51.6 | 0.74 | 20.3 | 0.79 | 34.0 | 0.84 | 57.6 | 0.90 |
| 1.1 | 48.1 | 1.13 | 17.0 | 1.12 | 30.9 | 1.08 | 57.5 | 0.91 |

10.5 Various Ionophores for K+ and Na+

An experiment was performed to study the efficacy of ionophores other than the valinomycin of Examples 10.1–10.4. Specifically, the ionophore Kryptofix ® 222 was used to make a test means specific for K+ and the ionophore Kryptofix K 221 was used for a Na+ specific test means.

A solution was prepared containing the following ingredients

| Component | Quantity | Final Concentration (g/100 mls solution) |
|---|---|---|
| PVC | 38.40 mg | 3.84 |
| DPP | 64.80 mg | 6.48 |
| Ionophore | 2.40 mg | 0.24 |
| THF | 0.935 ml | 93.50 |
| Total value | 1 ml | 100 ml |

Test means were prepared by the procedure described in Example 10.1.

Two series of test samples were prepared for use in assessing the test means for $K^+$ and $Na^+$. One set of samples contained KCl in aqueous 5 mM Erythrosin B and 20 mM tris-Cl (pH 7.2) to provide $K^+$ Concentrations of 0, 0.1, 0.3, 1.0, 3.0 and 30 mM. The second set of test samples contained NaCl instead of KCl, and were prepared at the same concentrations. These solutions were tested in triplicate and the mean values are reported below. The reflectance readings and their corresponding ion concentrations are tabulated in Table 6 and 7.

The results indicate that the ionophore Kryptofix 222 demonstrates a specific affinity for $K^+$ (Table 6), and a test means incorporating it provides a useful tool for quantitative analysis of potassium ion. Similarly, Kryptofix 221 (Table 7) provides a test means specific for, and capable of providing quantitative results for sodium ion.

TABLE 6

| Actual $K^+$ (mM) | % R | Observed $K^+$ (mM) | Actual $Na^+$ (mM) | % R | Observed $Na^+$ (mM) |
|---|---|---|---|---|---|
| 0 | 54.1 | 0.04 | 0 | 54.6 | 0.03 |
| 0.1 | 50.6 | 0.1 | 0.1 | 53.4 | 0.05 |
| 0.3 | 46.1 | 0.25 | 0.3 | 53.3 | 0.05 |
| 1.0 | 28.1 | 1.0 | 1.0 | 54.3 | 0.06 |

TABLE 6-continued

| Actual $K^+$ (mM) | % R | Observed $K^+$ (mM) | Actual $Na^+$ (mM) | % R | Observed $Na^+$ (mM) |
|---|---|---|---|---|---|
| 3.0 | 9.97 | 5.2 | 3.0 | 51.5 | 0.08 |

TABLE 7

| Actual $[K^+]$(mM) | % R | Observed $[K^+]$(mm) | Actual $[Na^+]$(mm) | % R | Observed $[Na^+]$ (mM) |
|---|---|---|---|---|---|
| 0 | 54.7 | .10 | 0 | 54.6 | .16 |
| .1 | 56.3 | 0 | .1 | 54.7 | .10 |
| .3 | 54.2 | .18 | .3 | 52.5 | .47 |
| 1.0 | 54.7 | .10 | 1.0 | 47.8 | 1.4 |
| 3.0 | 57.9 | 0 | 3.0 | 30.2 | 8.4 |
| 10.0 | 56.6 | .14 | 10.0 | 28.0 | 10 |
| 30 | 53.6 | .31 | 30.0 | 18.6 | 21.5 |

What is claimed is:

1. A method useful for the determination of a specific ion in an aqueous test sample, comprising the steps of:
    (a) adding a counterion reporter substance to an aqueous test sample,
    (b) contacting the counterion containing sample with a surface of a test means comprising a substantially nonpolar, nonporous, polymer carrier matrix incorporated with an ionophore capable of selectively forming a complex with a specific ion to be determined in the sample,
    (c) removing any unassociated counterion from the surface of the test means, and
    (d) determining a detectable optical response associated with the test means.

2. The method of claim 1 in which the determining step is accomplished by measuring the reflectance or absorbance of the test means.

3. The method of claim 1 in which a water impervious support is affixed to a surface of the test means which is opposite the surface which contacts the sample.

4. The method of claim 1 in which the sample is serum and the specific ion to be determined is potassium.

* * * * *